US012616387B2

(12) United States Patent
Doelman et al.

(10) Patent No.: US 12,616,387 B2
(45) Date of Patent: May 5, 2026

(54) DERIVATION OF PHYSIOLOGICAL PARAMETERS FROM A RADAR SIGNAL

(71) Applicant: Neteera Technologies LTD., Tel Aviv (IL)

(72) Inventors: Reinier Doelman, Jerusalem (IL); Ehud Fishler, Shoham (IL)

(73) Assignee: Neteera Technologies LTD., Tel Aviv (IL)

( * ) Notice: Subject to any disclaimer, the term of this patent is extended or adjusted under 35 U.S.C. 154(b) by 328 days.

(21) Appl. No.: 18/573,051

(22) PCT Filed: Jun. 26, 2022

(86) PCT No.: PCT/IL2022/050682
§ 371 (c)(1),
(2) Date: Dec. 21, 2023

(87) PCT Pub. No.: WO2023/275863
PCT Pub. Date: Jan. 5, 2023

(65) Prior Publication Data
US 2024/0293037 A1      Sep. 5, 2024

Related U.S. Application Data

(60) Provisional application No. 63/216,005, filed on Jun. 29, 2021.

(51) Int. Cl.
*A61B 5/024*          (2006.01)
*A61B 5/00*           (2006.01)
(Continued)

(52) U.S. Cl.
CPC ............ *A61B 5/02444* (2013.01); *A61B 5/05* (2013.01); *A61B 5/7221* (2013.01);
(Continued)

(58) Field of Classification Search
CPC .............. A61B 5/1102; A61B 5/02116; A61B 5/02405; A61B 5/02444; A61B 5/029;
(Continued)

(56) References Cited

U.S. PATENT DOCUMENTS

2018/0235481 A1      8/2018   Liu et al.
2020/0113445 A1*     4/2020   Gigie ..................... G16H 40/67
(Continued)

OTHER PUBLICATIONS

Novel methods for noncontact heart rate measurement: A feasibility study. IEEE transactions on instrumentation and measurement. 2013. 63.4: 838-847.# KRANJEC. Jure et al. (Nov. 4, 2013).
(Continued)

*Primary Examiner* — Keith M Raymond
*Assistant Examiner* — Milton Truong
(74) *Attorney, Agent, or Firm* — Renner, Otto, Boisselle & Sklar, LLP

(57) ABSTRACT

Apparatus and methods are described including deriving a subject's heart rate from in-phase and the quadrature signals received by a radar. The in-phase and quadrature signals are processed to generate two or more outputs using two or more respective methods. For each of the two or more outputs, for each of a plurality of time segments, the subject's heart rate is derived from the filtered signal, and quality scores are assigned to the subject's heart rate as derived for each of the plurality of time segments from each of the two or more outputs. At least partially based upon the quality scores, the subject's heart rate is derived using the output of one of the methods. Other applications are also described.

20 Claims, 2 Drawing Sheets

(51) Int. Cl.
    *A61B 5/05*         (2021.01)
    *G01S 7/35*         (2006.01)
    *G01S 7/41*         (2006.01)

(52) U.S. Cl.
    CPC .......... *A61B 5/7225* (2013.01); *A61B 5/7278*
        (2013.01); *G01S 7/354* (2013.01); *G01S 7/358*
                (2021.05); *G01S 7/415* (2013.01)

(58) Field of Classification Search
    CPC ....... A61B 5/05; A61B 5/0507; A61B 5/1107;
           A61B 5/1126; A61B 5/7221; A61B
        5/7225; A61B 5/7228; A61B 5/725; A61B
        5/7257; A61B 5/7278; G01S 13/88; G01S
        7/2886; G01S 7/354; G01S 7/358; G01S
                          7/415
    See application file for complete search history.

(56)                References Cited

U.S. PATENT DOCUMENTS

2020/0155011 A1*   5/2020   Park ..................... A61B 5/0507
2021/0022713 A1*   1/2021   Khasnobish ........ G01S 15/8977

OTHER PUBLICATIONS

Automatic signal quality index determination of radar-recorded heart sound signals using ensemble classification. IEEE transactions on biomedical engineering. 2019. 67.3: 773-785.# Shi. Kilin et al. (Jun. 5, 2019).
International Search Report for corresponding application No. PCT/IL2022/050682 mailed Oct. 26, 2022.

* cited by examiner

DERIVATION OF PHYSIOLOGICAL PARAMETERS FROM A RADAR SIGNAL

This application is a national phase of International Application No. PCT/IL2022/050682 filed Jun. 26, 2022, which claims the benefit of United States of America Application No. 63/216,005 filed Jun. 29, 2021, each of which is hereby incorporated herein by reference in its entirety.

FIELD OF THE INVENTION

Some applications of the presently disclosed subject matter relate generally to the derivation of a subject's physiological parameters in a non-invasive manner, and, in particular, to using a non-contact radar to derive a subject's heart rate.

BACKGROUND

There are a variety of methods that can be used for measuring a subject's physiological parameters (such as heart rate) in a non-invasive and/or non-contact manner. For example, a radar system can be used to detect motion of the subject without contacting the subject. A challenge associated with the detection of a subject's physiological parameters (such as heart rate) when using such systems is the removal of unrelated artifacts that are present within the subject's motion signal. For example, artifacts may be present within the signal as a result of instrument noise, muscle spasms, external or subject motion artifacts, and/or signal bias drift. The presence of noise within the radar signal may result in a such a system presenting the wrong heart rate value or no heart rate value at all.

SUMMARY OF EMBODIMENTS

In accordance with some applications of the present invention, a radar is configured to detect physiological parameters of a subject in a non-invasive and non-contact manner. For some applications, the radar is a frequency-modulated radar, for example, a frequency-modulated continuous-wave radar. For some applications, the radar transmitter is configured to transmit a signal having a frequency of between 500 MHz and 15 GHz, e.g., between 500 MHz and 2 GHz, or between 2 GHz and 10 GHz. Typically, a receiver of the radar detects a reflection of the signal, a portion of which is reflected from the subject's body, and the computer processor analyzes the transmitted and the received signals to thereby detect motion of the subject's body and derive physiological parameters of the subject based upon the motion (micro-motion) of the subject's body.

For some applications, the computer processor is configured to periodically sample the signals from the radar as measured over a given time period (or over an entire session) and to derive a representative value of the physiological parameter for the time period. For some applications, in order to derive a representative value of the physiological parameter for the time period, the computer processor analyses a radar signal using an algorithm as described hereinbelow. Typically, by applying the algorithm as described hereinbelow, the computer processor optimizes the accuracy of the derived heart rate by first determining a processing method that yields the highest quality measure of the heart rate and using that processing method for deriving the heart rate.

As noted above, the algorithm described hereinbelow is typically applied in order to derive a representative value of a subject's heart rate over a given time period. Thus, the algorithm may be referred to as a periodic algorithm in that it is run periodically in order to derive a representative value of a subject's heart rate over a given time period. For some applications, in addition to deriving a representative value of a subject's heart rate over a given time period (e.g., using the periodic algorithm), the computer processor is configured to run a continuous algorithm that is configured to determine the subject's heart rate in real time, as data is received by the radar. For some applications, the periodic algorithm is used to validate and/or correct the heart rate as determined using the continuous algorithm, as described in further detail hereinbelow. For example, the continuous algorithm may be steered toward detecting a frequency range that corresponds to the representative heart rate as detected using continuous algorithm.

There is therefore provided, in accordance with some applications of the present invention, apparatus for use with a radar, the apparatus including:

at least one computer processor configured to:

receive in-phase and quadrature signals from the radar;

derive a subject's heart rate from the in-phase and the quadrature signals by:

processing the in-phase and quadrature signals to generate two or more outputs using two or more respective methods, the two or more methods including at least two out of: (a) calculating a phase of each of the in-phase and the quadrature signals with respect to a center for each point in time, (b) calculating a complex signal based upon the in-phase and the quadrature signals, and (c) calculating a linear combination of the in-phase and quadrature signals;

for each of the two or more outputs:

filtering the signal to at least partially dampen frequencies that are below a minimum frequency; and for each of a plurality of time segments, deriving the subject's heart rate from the filtered signal;

assigning quality scores to the subject's heart rate as derived for each of the plurality of time segments from each of the two or more outputs; and at least partially based upon the quality scores, selecting to derive the subject's heart rate using the output of either method (a), (b), or (c); and output the subject's heart rate, as derived using the selected output.

In some applications, the at least one computer processor is configured to filter the signal to at least partially dampen frequencies that are above a maximum frequency and below a minimum frequency.

In some applications, the at least one computer processor is configured to filter the signal to remove frequencies that are below the minimum frequency.

In some applications, the at least one computer processor is configured to filter the signal to remove frequencies that are above a maximum frequency and below a minimum frequency.

In some applications, based upon the outputted subject's heart rate, the at least one computer processor is configured to derive one or additional physiological parameters of the subject, the one or additional physiological parameters of the subject being selected from the group consisting of: heart rate variability, heart rate interval, pulse wave velocity, blood pressure, mean arterial pressure, systolic pressure, diastolic pressure, vascular resistance, pulse pressure variability, stroke volume, and stroke volume variability.

In some applications, based upon the outputted subject's heart rate, the at least one computer processor is configured to derive a state of the subject, the state of the subject being selected from the group consisting of: a stressed state, a fatigued state.

In some applications, the at least one computer processor is configured to process the in-phase and quadrature signals to generate three or more outputs using three or more respective methods, the three or more respective methods including (a) calculating a phase of each of the in-phase and the quadrature signals with respect to a center for each point in time, (b) calculating a complex signal based upon the in-phase and the quadrature signals, and (c) calculating a linear combination of the in-phase and quadrature signals.

In some applications, the at least one computer processor is configured to derive the subject's heart rate from the filtered signal for each of the plurality of time segments by calculating a power spectrum using the filtered signal, for each of the plurality of time segments.

In some applications, the at least one computer processor is configured to derive the subject's heart rate from the filtered signal for each of the plurality of time segments by deriving the subject's heart rate from the filtered signal, for each of a plurality of overlapping time segments.

In some applications, the at least one computer processor is configured to derive the subject's heart rate from the filtered signal for each of the plurality of time segments by deriving the subject's heart rate from the filtered signal, for each of a plurality of non-overlapping time segments.

In some applications, the at least one computer processor is configured to derive the subject's heart rate from the filtered signal for each of the plurality of time segments by deriving the subject's heart rate from the filtered signal, for each of a plurality of time segments having a duration of at least 2 seconds.

In some applications, the at least one computer processor is configured to derive the subject's heart rate from the filtered signal for each of the plurality of time segments by deriving the subject's heart rate from the filtered signal, for each of a plurality of time segments having a duration of between 5 seconds and 15 seconds.

In some applications, the radar includes a continuous-wave radar system, and the at least one computer processor is configured to receive the in-phase and quadrature signals from the continuous-wave radar system.

In some applications, the radar includes a frequency-modulated, continuous-wave radar system, and the at least one computer processor is configured to receive the in-phase and quadrature signals from the frequency-modulated, continuous-wave radar system.

In some applications, the at least one computer processor is configured to output the subject's heart rate as derived using the selected output by, using the selected output, deriving the subject's heart rate from the filtered signal for each of the time segments, and calculating a weighted average of the subject's heart rate as derived for each of the time segments.

In some applications, the at least one computer processor is configured to calculate the weighted average of the power spectra of the time segments by assigning weights to respective time segments based upon the quality scores of the time segments.

In some applications, the at least one computer processor is configured, at least partially based upon the quality scores as derived for each of the plurality of time segments, to select a frequency range to utilize for filtering the signal to at least partially dampen frequencies that are below the minimum frequency.

In some applications, the at least one computer processor is configured to perform a grid search over the two or more outputs and over a plurality of frequency ranges to utilize for filtering the signal to at least partially dampen frequencies that are below the minimum frequency, and to select to derive the subject's heart rate using a given methodology based upon the grid search.

In some applications, the at least one computer processor is configured to at least partially dampen frequencies that are below the minimum frequency by filtering the signal to at least partially dampen frequencies that are below 5 Hz.

In some applications, the at least one computer processor is configured to at least partially dampen frequencies that are below the minimum frequency by filtering the signal to at least partially dampen frequencies that are below 8 Hz.

In some applications, the at least one computer processor is configured to at least partially dampen frequencies that are below the minimum frequency by filtering the signal to at least partially dampen frequencies that are below 5 Hz and above 50 Hz.

In some applications, the at least one computer processor is configured to at least partially dampen frequencies that are below the minimum frequency by filtering the signal to at least partially dampen frequencies that are below 8 Hz and above 40 Hz.

In some applications, the at least one computer processor is configured to assign quality scores to the subject's heart rate as derived for each of the plurality of time segments from each of the two or more outputs by assigning quality scores based upon the presence of a prominent peak within a power spectrum corresponding to that time segment from each of the two or more outputs.

In some applications, the at least one computer processor is configured to assign quality scores to the subject's heart rate as derived for each of the plurality of time segments from each of the two or more outputs by assigning high quality scores to time segments having a prominent peak within the power spectrum and low quality scores to time segments having a smeared signal.

In some applications, the at least one computer processor is configured to assign quality scores to the subject's heart rate as derived for each of the plurality of time segments from each of the two or more outputs by assigning high quality scores to time segments having a prominent peak within the power spectrum and low quality scores to time segments in which the signal is indicative of large body motion of the subject There is further provided, in accordance with some applications of the present invention, a method including:

receiving in-phase and quadrature signals using a radar; and deriving a subject's heart rate from the in-phase and the quadrature signals by:

processing the in-phase and quadrature signals to generate two or more outputs using two or more respective methods, the two or more methods including at least two out of: (a) calculating a phase of each of the in-phase and the quadrature signals with respect to a center for each point in time, (b) calculating a complex signal based upon the in-phase and the quadrature signals, and (c) calculating a linear combination of the in-phase and quadrature signals;

for each of the two or more outputs:

filtering the signal to at least partially dampen frequencies that are below a minimum frequency; and for each of a plurality of time segments, deriving the subject's heart rate from the filtered signal;

assigning quality scores to the subject's heart rate as derived for each of the plurality of time segments from each of the two or more outputs; and at least partially based upon the quality scores, selecting to derive the subject's heart rate using the output of either method (a), (b), or (c); and outputting the subject's heart rate, as derived using the selected output.

There is further provided, in accordance with some applications of the present invention, a computer software product, for use with a radar, the computer software product including a non-transitory computer-readable medium in which program instructions are stored, which instructions, when read by a computer cause the computer to perform the steps of:

receiving in-phase and quadrature signals from the radar;

deriving a subject's heart rate from the in-phase and the quadrature signals by:

processing the in-phase and quadrature signals to generate two or more outputs using two or more respective methods, the two or more methods including at least two out of: (a) calculating a phase of each of the in-phase and the quadrature signals with respect to a center for each point in time, (b) calculating a complex signal based upon the in-phase and the quadrature signals, and (c) calculating a linear combination of the in-phase and quadrature signals;

for each of the two or more outputs:

filtering the signal to at least partially dampen frequencies that are below a minimum frequency; and for each of a plurality of time segments, deriving the subject's heart rate from the filtered signal;

assigning quality scores to the subject's heart rate as derived for each of the plurality of time segments from each of the two or more outputs; and at least partially based upon the quality scores, selecting to derive the subject's heart rate using the output of either method (a), (b), or (c); and outputting the subject's heart rate, as derived using the selected output.

The present invention will be more fully understood from the following detailed description of embodiments thereof, taken together with the drawings, in which:

DETAILED DESCRIPTION OF EMBODIMENTS

Figure 1:
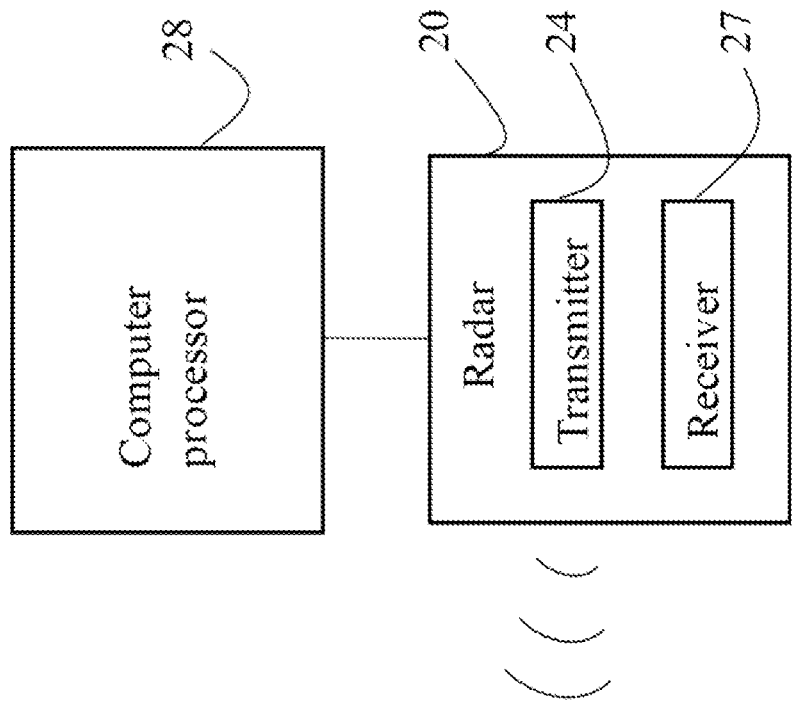
FIG. 1 is a schematic illustration of a radar that is configured to detect physiological parameters of a subject in a non-invasive and non-contact manner, in accordance with some applications of the present invention.
Figure 1:
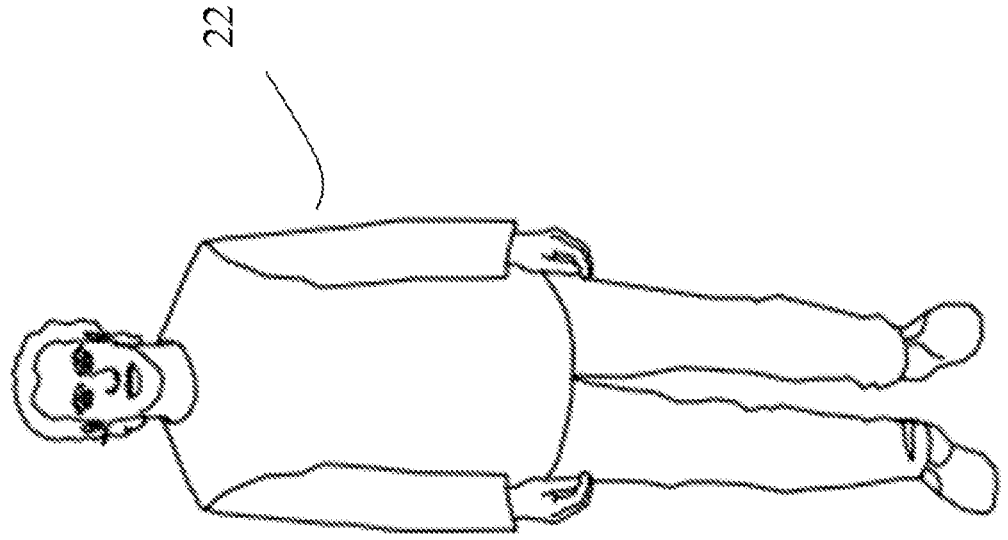

Reference is now made to FIG. 1, which is a schematic illustration of a radar 20 that is configured to detect physiological parameters of a subject 22 in a non-invasive and non-contact manner, in accordance with some applications of the present invention. Typically, the radar includes a transmitter 24 and a receiver 27. Further typically, a computer processor 28 processes signals that are transmitted by transmitter 24 and received by receiver 27, to thereby derive physiological parameters of the subject. For some applications, the radar is a frequency-modulated radar, for example, a frequency-modulated continuous-wave radar. For some applications, the transmitter is configured to transmit a signal having a frequency of between 500 MHz and 15 GHz, e.g., between 500 MHz and 2 GHz, or between 2 GHz and 10 GHz. For some applications, the transmitter is configured to transmit a signal having a frequency in the THz range and/or the sub-THz range. For some such applications, the transmitter is configured to transmit a signal having a frequency of between 1 GHz and 1 THz, such as between 50 GHz and 1 THz, or between 50 GHz and 500 GHz.

Typically, the receiver detects a reflection of the signal, a portion of which is reflected from the subject's body, and the computer processor analyzes the transmitted and the received signals to thereby detect motion of the subject's body and derive physiological parameters of the subject based upon the motion of the subject's body. The subject typically includes at least one individual within a given space that the radar is configured to monitor, such as a patient, an adult, an infant, a toddler, a baby, a child, an elderly subject, an occupant of a vehicle, a driver of a vehicle, and/or a passenger of a vehicle. For some applications, the computer processor is configured to derive respective body motions of two or more subjects within the space and to distinguish between body motions of respective subjects. Typically, whether the system is used with a single subject or multiple subjects, the computer processor is configured to isolate a signal that is indicative of the body motion of each subject from other components within the received signal.

For some applications, the computer processor is configured to derive one or more of the following physiological parameters from the signal that is indicative of the subject's body motion: heart rate, heart rate variability, heart rate amplitude, heart rate amplitude variability, respiration rate, respiration rate variability, respiration amplitude, respiration amplitude variability, ballistocardiogram, ballistocardiogram amplitude variability, pulse wave velocity, blood pressure (e.g., mean arterial pressure, systolic pressure, and/or diastolic pressure), vascular resistance, body temperature, pulse pressure variability, stroke volume, and/or stroke volume variability. For some applications, the computer processor is configured to derive the subject's ballistocardiogram signal from the signal that is indicative of the subject's body motion, and is configured to derive additional physiological parameters (such as heart rate, heart rate variability, heart rate amplitude, heart rate amplitude variability, respiration rate, respiration rate variability, respiration amplitude, respiration amplitude variability, ballistocardiogram amplitude variability, pulse wave velocity, blood pressure (e.g., mean arterial pressure, systolic pressure, and/or diastolic pressure), vascular resistance, body temperature, pulse pressure variability, stroke volume, and/or stroke volume variability) from the subject's ballistocardiogram signal. For some applications, the computer processor is configured to determine that the subject has a medical condition, is undergoing a clinical episode, and/or is predicted to undergo a clinical episode, based upon one or more of the aforementioned physiological parameters.

Figure 2:
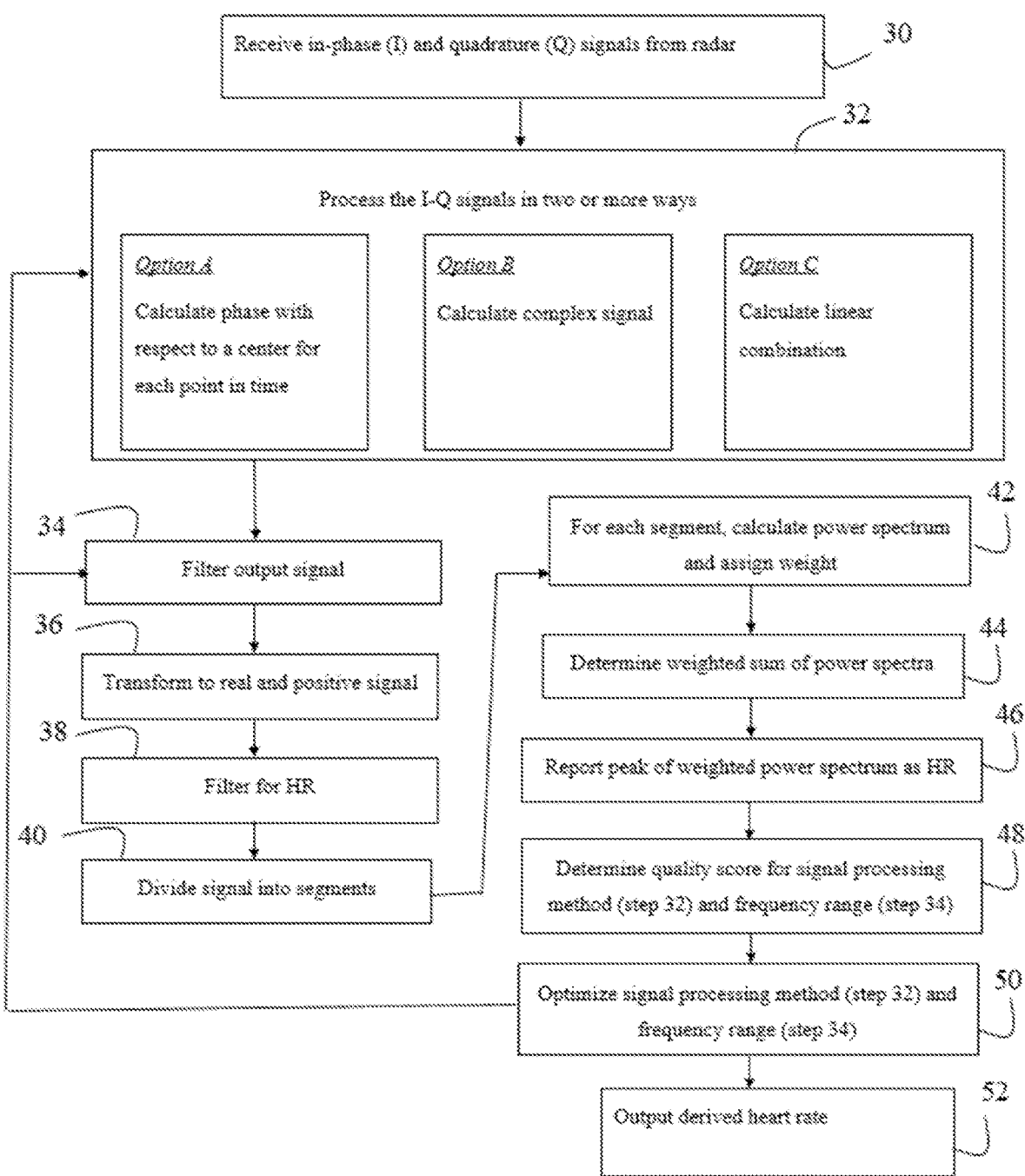
FIG. 2 is a flowchart showing steps of a heart-rate-derivation method performed in accordance with some applications of the present invention.

For some applications, over a given monitoring session, the computer processor is configured to continuously derive one or more of the above-described physiological parameters in real time. Alternatively or additionally, the computer processor is configured to periodically sample the signals from the radar as measured over a given time period (or over an entire session) and to derive a representative value of the physiological parameter for the time period. For some applications, in order to derive a representative value of the physiological parameter for the time period, the computer processor analyses a radar signal using an algorithm as described herein. For example, in order to derive a representative value of a subject's heart rate over a given time period, an algorithm as described with reference to FIG. 2 may be applied. Typically, by applying the algorithm as described with reference to FIG. 2, the computer processor optimizes the accuracy of the derived heart rate by first determining a processing method that yields the highest quality measure of the heart rate and using that processing method for deriving the heart rate. It is noted that the algorithm described with reference to FIG. 2 is applicable to the derivation of a subject's heart rate. However, the scope of the present application includes applying a similar algorithm to the derivation of a different physiological parameter, mutatis mutandis.

Reference is now made to FIG. 2, which is a flowchart showing steps of a heart-rate-derivation algorithm that are performed in accordance with some applications of the present invention. Typically, in a first step 30, computer processor 28 receives in-phase (I) and quadrature (Q) signals from radar 20. (The combination of the in-phase and quadrature signals are referred to hereinafter as the "I-Q signal.") Computer processor 28 may receive multiple I-Q signals (I1, Q2, I2, Q2, . . . ) from radar 20, depending on the mode in which radar 20 operates or the radar design. In a subsequent step 32, the computer processor processes the I-Q signal in two or more ways. Typically, the computer processor processes the I-Q signal in three or more ways. For some applications, a first way in which the computer processor processes the I-Q signal ("Option A") is by calculating the phase of the I-Q signal, with respect to a center (e.g., a calculated or reference center), for each point in time. Alternatively or additionally, the amplitude of the I-Q signal is calculated for each point in time. Typically, the reference center is calculated by taking the mean of the extrema of the I-Q signal, or using a general circle-fitting algorithm. The amplitude and/or phase of the I-Q signal, with respect to this reference center is then calculated for each point in time. For some applications, a second way in which the computer processor processes the I-Q signal ("Option B") is by calculating a complex signal based upon the in-phase and the quadrature signals, with the complex signal typically being defined as "I+jQ", or "I-jQ" (where j is the imaginary unit, satisfying the equation j*j=−1) or another combination of I and Q into a complex number. For some applications, a third way in which the computer processor processes the I-Q signal ("Option C") is by calculating a linear combination of the in-phase and quadrature signals, with the linear combination typically being defined as: "a*I+b*Q", or alternatively: a*(I1+Q1)+b*(I2+Q2)+ . . . etc, where a and b are real, scalar numbers. As noted above, for some applications, the computer processor performs each of Options A, B, and C. Alternatively, the computer processor performs any combination of two of the three options. For some applications, the computer processor processes the I-Q signal using alternative or additional processing methods.

Typically, the computer processor takes the output from each of the processing options from step 32 and applies each of steps 34-50 to each of these outputs. Typically, in step 34, the computer processor applies a filter to each of the outputs. Further typically, a high-pass linear time-invariant filter, or a linear time-invariant bandpass filter is applied. For some applications, the filter is applied such as to remove frequencies falling out of a range of 5-50 Hz, e.g., 8-40 Hz, or a frequency range within the aforementioned range. Alternatively, a high-pass linear time-invariant filter having cutoff frequency of 5 Hz or above (e.g., 8 Hz or above) is applied, such that there is no removal of signals above a given frequency, since such signals are typically not present or very strong in the first instance. It is noted that the frequency range is selected to correspond to a frequency component in the signal that is high relative to heart rate, but which is known to be indicative of heart rate. Typically, the frequency range that is applied in step 34 is refined iteratively, as described in further detail hereinbelow with reference to step 50.

In step 36, the output of step 34 (for each of the options from step 32) is transformed to a real and positive signal. Thus, if the output of step 34 is a signal y, then this signal is typically transformed to a signal x, based upon the equation:

$$x=|y|\char`^p, \text{ where } p \text{ is a positive number.}$$

Thus, whatever the characteristics of the signal y (the output of step 34), the signal x (the output of step 36) is always real and positive.

In step 38, a filter is applied to the output from step 36, in order to reject frequencies below the lowest heart rate of interest. For example, a high-pass filter with cutoff frequency of 30 beats-per-minute (i.e., "BPM") (e.g., 40 BPM) may be applied. For some applications, a filter is applied to remove frequencies falling outside of the range of 30-250 BPM (e.g., 40-200 BPM) or a frequency range that falls within the aforementioned range. Typically, the filter that is applied in step 38 is configured to remove frequencies that are outside of the normal range of a human heart rate.

In step 40, the signal is divided into segments of time. For some such applications, there is overlap between the segments. Alternatively, the segments are applied such that there is no overlap. Typically, the segments correspond to time periods of at least 2 seconds, for example, between 2 seconds and 30 seconds, e.g., between 5 second and 15 seconds.

In step 42, the power spectrum of the signal for each segment is calculated, and is typically normalized (e.g., by being normalized to a unit norm). Further typically, each segment gets scored a weight, which represents a quality score of the signal in the segment. Typically, the weight is calculated such as to reflect how "clean" the heart rate signal is, for example, by determining the extent to which is there a prominent peak in the power spectrum. For some applications, the 'prominence' of a peak is computed using standard software, such as the Python library 'scipy.signal.find_peaks'. Typically, disturbance in the signal in a given time segment (for example, caused by large body motion during the time segment) smears the signal for that segment, and obscures the effect of heartbeats on the body motion, resulting in it receiving a low weight. For some applications, low weights are applied to such segments. In this manner, the contribution of such segments to the heart rate estimate is limited, such that the heart rate estimate is more accurate than if all segments were to be assigned equal weights, ceteris paribus. Typically, a weight is computed for a given segment based on the calculated prominence of a peak within that segment. For example, segments with very prominent peaks may be assigned a weight of close to 1, while relatively smeared segments (i.e., those without a clearly prominent peak) may be assigned a weight close to or equal to zero.

In step 44, the weighted sum of the power spectra for a plurality of time segments is computed, and in step 46, the peak in the weighted power spectra sum is reported as the heart rate.

In step 48, for a given signal-processing methodology (i.e., a given signal-processing method (used in step 32) and a given frequency range used by the high-pass or bandpass filter (in step 34)), a quality score for the reported heart rate is determined. For some applications, the quality score is determined by ranking the scores of time segments that were analyzed using that methodology, and determining the weight of a time segment having a given ranking within the time segments. For example, the weights of the time segments may be ranked into percentiles, and the weight of the time segment that falls at a given percentile may be used to indicate the quality score for the methodology. By way of illustration, the weight of the time segment that falls at the $80^{th}$, $90^{th}$, or $95^{th}$ percentile may be used to indicate the quality score for the methodology. Alternatively or additionally, a different method of determining the quality score may be used. For example, the lengths of time over which a good quality signal was continuously measured using each of the methodologies may be measured.

In step 50, based upon the output of step 48, a signal-processing method (used in step 32) and frequency range to be used by the high-pass or bandpass filter (in step 34) is selected, typically to select the methodology having the highest quality score or a minimal pre-defined score as determined in step 48. For some applications, a grid search is performed over the options for signal-processing methods (used in step 32) and the frequency ranges used by the bandpass filter (in step 34).

In step 52, based on the output of step 50, a signal-processing method (used in step 32) and/or the frequency range used by the bandpass filter (in step 34) is selected, and the heart rate as reported in step 44 for the chosen methodology is output as the heart rate.

It is noted that the algorithm described with reference to FIG. 2 includes step 32, in which the I-Q signals are processed in two or more ways, and step 50 includes optimizing both the signal processing method (step 32) and frequency range (step 34). For some applications, a generally similar method is performed, but in step 32 the I-Q signals are processed in only one way, and in step 50 only the frequency range used by the high-pass or bandpass filter in step 34 is optimized, mutatis mutandis.

As noted above, the steps described with reference to FIG. 2 are typically applied in order to derive a representative value of a subject's heart rate over a given time period. Typically, by applying the algorithm as described with reference to FIG. 2, the computer processor optimizes the accuracy of the derived heart rate by first determining a processing method that yields the highest quality measure of the heart rate and using that processing method for deriving the heart rate. Although the algorithm described with reference to FIG. 2 is applicable to the derivation of a subject's heart rate, the scope of the present application includes applying a similar algorithm to the derivation of a different physiological parameter, such as respiration rate, mutatis mutandis. For some applications, based upon the subject's heart rate as derived using the steps described herein, the computer processor is configured to derive one or more additional physiological parameters, such as heart rate variability, heart rate interval, pulse wave velocity, blood pressure (e.g., mean arterial pressure, systolic pressure, and/or diastolic pressure), vascular resistance, pulse pressure variability, stroke volume, and/or stroke volume variability), and/or a state of the subject (such as stress, fatigue, etc.).

As noted above, the steps described with reference to FIG. 2 are typically applied in order to derive a representative value of a subject's heart rate over a given time period. Thus, the algorithm described with reference to FIG. 2 may be referred to as a periodic algorithm in that it is run periodically in order to derive a representative value of a subject's heart rate over a given time period. For some applications, in addition to deriving a representative value of a subject's heart rate over a given time period (e.g., using the periodic algorithm), the computer processor is configured to run a continuous algorithm that is configured to determine the subject's heart rate in real time, as data is received by the radar. Typically, the continuous algorithm analyzes different frequency components within the radar signal from those analyzed in the periodic algorithm. Further typically, the continuous algorithm analyzes frequencies below 3 Hz. For some applications, analyzing frequencies below 3 Hz can lead to errors, due to the algorithm interpreting a different signal as being the subject's heart rate signal. For example, a high respiration rate, or a harmonic of the heart rate (e.g., a signal at exactly two or three times the heart rate) may be interpreted as being the subject's heart rate signal. For some applications, the periodic algorithm is therefore used to validate and/or adjust the heart rate as determined using the continuous algorithm. For example, at a given time interval (e.g., once every 10 seconds, once every 30 seconds, or once a minute), the heart rate as determined using the continuous algorithm may be compared to the representative heart rate determined using the periodic algorithm. If a substantial discrepancy is detected (e.g., a difference or a ratio that exceeds a threshold), the continuous algorithm may be adjusted accordingly. For example, the continuous algorithm may be steered toward detecting a frequency range that corresponds to the representative heart rate as detected using continuous algorithm.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processor 28 is typically a hardware device programmed with computer program instructions to produce a special purpose computer. For example, when programmed to perform the algorithms described herein, computer processor 28 typically acts as a special purpose sample-analysis computer processor. Typically, the operations described herein that are performed by computer processor 28 transform the physical state of a memory, which is a real physical article, to have a different magnetic polarity, electrical charge, or the like depending on the technology of the memory that is used.

The apparatus and methods described herein may be used in conjunction with apparatus and methods described in any one of the following patents or patent applications, all of which are incorporated herein by reference:

U.S. Pat. No. 10,224,363 to Goldberger,
US 2018/0256082 to Steinberg,
US 2020/0313277 to Tomo,
WO 20/012455 to Steinberg,
WO 20/202159 to Steinberg,
WO 20/250233 to Steinberg, and WO 21/028915 to Moskovich.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for deriving a heart rate of a subject comprising the steps of:

receiving in-phase and quadrature signals using a radar; and deriving a subject's heart rate from the in-phase and the quadrature signals by:

processing the in-phase and quadrature signals to generate two or more outputs using two or more respective methods, the two or more methods comprising at least two out of:

(a) calculating a phase of each of the in-phase and the quadrature signals with respect to a center for each point in time, (b) calculating a complex signal based upon the in-phase and the quadrature signals, and (c) calculating a linear combination of the in-phase and quadrature signals; for each of the two or more outputs:

filtering the outputsignal to at least partially dampen frequencies that are below a minimum frequency to generate a filtered signal;

dividing the filtered signal into a plurality of time segments; and for each of the plurality of time segments, deriving the subject's heart rate from the filtered signal;

assigning quality scores to the subject's heart rate as derived for each of the plurality of time segments from each of the two or more outputs; and at least partially based upon the quality scores, selecting to derive the subject's heart rate using the output of either method (a), (b), or (c); and outputting the subject's heart rate, as derived using the selected output.

2. The method according to claim 1, wherein filtering the output to at least partially dampen frequencies that are below a minimum frequency comprises at least one filtering selected from the group consisting of:

filtering the output to at least partially dampen frequencies that are above a maximum frequency and below a minimum frequency;

filtering the output to remove frequencies that are below the minimum frequency; filtering the signaloutput to remove frequencies that are above a maximum frequency and below a minimum frequency;

filtering the output to at least partially dampen frequencies that are below 5 Hz;

filtering the output to at least partially dampen frequencies that are below 8 Hz;

filtering the output to at least partially dampen frequencies that are below 5 Hz and above 50 Hz; and filtering the output to at least partially dampen frequencies that are below 8 Hz and above 40 Hz.

3. The method according to claim 1, further comprising, based upon the outputted subject's heart rate, deriving one or additional physiological parameters of the subject, the one or additional physiological parameters of the subject being selected from the group consisting of: heart rate variability, heart rate interval, pulse wave velocity, blood pressure, mean arterial pressure, systolic pressure, diastolic pressure, vascular resistance, pulse pressure variability, stroke volume, and stroke volume variability.

4. The method according to claim 1, wherein for each of a plurality of time segments deriving the subject's heart rate from the filtered signal comprises, at least one operation selected from the group consisting of:

for each of a plurality of time segments, calculating a power spectrum using the filtered signal;

for each of a plurality of overlapping time segments, deriving the subject's heart rate from the filtered signal;

for each of a plurality of non-overlapping time segments, deriving the subject's heart rate from the filtered signal;

for each of a plurality of time segments having a duration of at least 2 seconds, deriving the subject's heart rate from the filtered signal; and for each of a plurality of time segments having a duration of between 5 seconds and 15 seconds, deriving the subject's heart rate from the filtered sign.

5. The method according to claims 1, wherein receiving in-phase and quadrature signals using a radar comprises receiving in-phase and quadrature signals using at least one of: a continuous-wave (CW) radar system; and a frequency-modulated continuous-wave (FMCW) radar system.

6. The method according to claims 1, wherein outputting the subject's heart rate as derived using the selected output comprises, using the selected output, deriving the subject's heart rate from the filtered signal for each of the time segments, and calculating a weighted average of the subject's heart rate as derived for each of the time segments.

7. The method according to claim 6, wherein calculating the weighted average of the power spectra of the time segments comprises assigning weights to respective time segments based upon the quality scores of the time segments.

8. The method according to claim 1, further comprising at least partially based upon the quality scores as derived for each of the plurality of time segments selecting a frequency range to utilize for filtering the output to at least partially dampen frequencies that are below the minimum frequency.

9. The method according to claim 8, wherein at least partially based upon the quality scores, selecting to derive the subject's heart rate using the output of either method (a), (b), or (c) comprises performing a grid search over the two or more outputs and over a plurality of frequency ranges to utilize for filtering the output to at least partially dampen frequencies that are below the minimum frequency, and selecting to derive the subject's heart rate using a given methodology based upon the grid search.

10. The method according to claims 1, wherein assigning quality scores to the subject's heart rate as derived for each of the plurality of time segments from each of the two or more outputs comprises at least one selected from the group consisting of:

assigning quality scores based upon the presence of a prominent peak within a power spectrum corresponding to that time segment from each of the two or more outputs;

assigning high quality scores to time segments having a prominent peak within the power spectrum and low quality scores to time segments having a smeared signal; and assigning high quality scores to time segments having a prominent peak within the power spectrum and low quality scores to time segments in which the signal is indicative of large body motion of the subject.

11. Apparatus for deriving a heart rate of a subject, for use with a radar, the apparatus comprising: at least one computer processor configured to:

receive in-phase and quadrature signals from the radar;

derive a subject's heart rate from the in-phase and the quadrature signals by:

processing the in-phase and quadrature signals to generate two or more outputs using two or more respective methods, the two or more methods comprising at least two out of:

(a) calculating a phase of each of the in-phase and the quadrature signals with respect to a center for each point in time, (b) calculating a complex signal based upon the in-phase and the quadrature signals, and (c) calculating a linear combination of the in-phase and quadrature signals;

for each of the two or more outputs:

filtering the output to at least partially dampen frequencies that are below a minimum frequency to generate a filtered signal;

dividing the filtered signal into a plurality of time segments; and for each of the plurality of time segments, deriving the subject's heart rate from the filtered signal;

assigning quality scores to the subject's heart rate as derived for each of the plurality of time segments from each of the two or more outputs; and at least partially based upon the quality scores, selecting to derive the subject's heart rate using the output of either method (a), (b), or (c); and output the subject's heart rate, as derived using the selected output.

12. The apparatus according to claim 11, wherein the at least one computer processor is configured to filter the output to at least partially dampen frequencies by at least one filtering selected from the group consisting of:

filtering the output to at least partially dampen frequencies that are above a maximum frequency and below a minimum frequency;

filtering the output to remove frequencies that are below the minimum frequency;

filtering the output to remove frequencies that are above a maximum frequency and below a minimum frequency;

filtering the output to at least partially dampen frequencies that are below 5 Hz;

filtering the output to at least partially dampen frequencies that are below 8 Hz;

filtering the output to at least partially dampen frequencies that are below 5 Hz and above 50 Hz; and filtering the output to at least partially dampen frequencies that are below 8 Hz and above 40 Hz.

13. The apparatus according to claim 11, wherein, based upon the outputted subject's heart rate, the at least one computer processor is configured to derive one or additional physiological parameters of the subject, the one or additional physiological parameters of the subject being selected from the group consisting of:

heart rate variability, heart rate interval, pulse wave velocity, blood pressure, mean arterial pressure, systolic pressure, diastolic pressure, vascular resistance, pulse pressure variability, stroke volume, and stroke volume variability.

14. The apparatus according to claim 11, wherein the at least one computer processor is configured to derive the subject's heart rate from the filtered signal for each of the plurality of time segments by at least one operation selected from the group consisting of:

calculating a power spectrum using the filtered signal, for each of the plurality of time segments;

deriving the subject's heart rate from the filtered signal, for each of a plurality of overlapping time segments;

deriving the subject's heart rate from the filtered signal, for each of a plurality of non-overlapping time segments;

deriving the subject's heart rate from the filtered signal, for each of a plurality of time segments having a duration of at least 2 seconds;

deriving the subject's heart rate from the filtered signal, for each of a plurality of time segments having a duration of between 5 seconds and 15 seconds.

15. The apparatus according to claims 11, wherein the radar includes at least one of: a continuous-wave (CW) radar system; and a frequency-modulated continuous-wave (FMCW) radar system, and wherein the at least one computer processor is configured to receive the in-phase and quadrature signals from at least one of: the continuous-wave (CW) radar system and the frequency- modulated continuous-wave (FMCW) radar system.

16. The apparatus according to claims 11, wherein the at least one computer processor is configured to output the subject's heart rate as derived using the selected output by, using the selected output, deriving the subject's heart rate from the filtered signal for each of the time segments, and calculating a weighted average of the subject's heart rate as derived for each of the time segments.

17. The apparatus according to claim 16, wherein the at least one computer processor is configured to calculate the weighted average of the power spectra of the time segments by assigning weights to respective time segments based upon the quality scores of the time segments.

18. The apparatus according to claim 11, wherein the at least one computer processoris configured, at least partially based upon the quality scores as derived for each of the plurality of time segments, to select a frequency range to utilize for filtering the output to at least partially dampen frequencies that are below the minimum frequency.

19. The apparatus according to claim 18, wherein the at least one computer processor is configured to perform a grid search over the two or more outputs and over a plurality of frequency ranges to utilize for filtering the output to at least partially dampen frequencies that are below the minimum frequency, and to select to derive the subject's heart rate using a given methodology based upon the grid search.

20. The apparatus according to claims 11, wherein the at least one computer processor is configured to assign quality scores to the subject's heart rate as derived for each of the plurality of time segments from each of the two or more outputs by at least one selected from the group consisting of:

assigning quality scores based upon the presence of a prominent peak within a power spectrum corresponding to that time segment from each of the two or more outputs;

assigning high quality scores to time segments having a prominent peak within the power spectrum and low quality scores to time segments having a smeared signal; and assigning high quality scores to time segments having a prominent peak within the power spectrum and low quality scores to time segments in which the signal is indicative of large body motion of the subject.

\* \* \* \* \*